US010234771B2

(12) United States Patent
Lin et al.

(10) Patent No.: US 10,234,771 B2
(45) Date of Patent: Mar. 19, 2019

(54) HHG SOURCE, INSPECTION APPARATUS AND METHOD FOR PERFORMING A MEASUREMENT

(71) Applicant: ASML Netherlands B.V., Veldhoven (NL)

(72) Inventors: Nan Lin, Eindhoven (NL); Arie Jeffrey Den Boef, Waalre (NL); Sander Bas Roobol, Veldhoven (NL); Simon Gijsbert Josephus Mathijssen, Rosmalen (NL); Niels Geypen, Lommel (BE)

(73) Assignee: ASML Netherlands B.V, Veldhoven (NL)

( * ) Notice: Subject to any disclaimer, the term of this patent is extended or adjusted under 35 U.S.C. 154(b) by 0 days.

(21) Appl. No.: 15/487,558

(22) Filed: Apr. 14, 2017

(65) Prior Publication Data
US 2017/0315456 A1  Nov. 2, 2017

(30) Foreign Application Priority Data
Apr. 28, 2016 (EP) ..................................... 16167512

(51) Int. Cl.
*G03F 7/20* (2006.01)
*G01B 11/24* (2006.01)
(Continued)

(52) U.S. Cl.
CPC .......... *G03F 7/70616* (2013.01); *G01B 11/24* (2013.01); *G01N 21/9501* (2013.01);
(Continued)

(58) Field of Classification Search
CPC ......... G01B 11/24; G02F 1/3551; G02F 1/37; G03F 7/70616; H01S 3/0092; H01S 3/1305; H01S 3/1625; H01S 3/1636
See application file for complete search history.

(56) References Cited

U.S. PATENT DOCUMENTS 6,014,252 A * 1/2000 Shafer ................ G02B 17/0657
359/208.1
9,347,890 B2 5/2016 Brown et al.
(Continued)

FOREIGN PATENT DOCUMENTS

TW        201537163 A    10/2015
WO   WO 2016/150957 A1   9/2016
(Continued)

OTHER PUBLICATIONS

Reinink J., "Pulse Shaping for High Harmonic Generation," Master Thesis in Applied Physics, University of Twente, 2013; 74 pages.
(Continued)

*Primary Examiner* — Tri T Ton
(74) *Attorney, Agent, or Firm* — Sterne, Kessler, Goldstein & Fox P.L.L.C.

(57) ABSTRACT

Disclosed is a method of performing a measurement in an inspection apparatus, and an associated inspection apparatus and HHG source. The method comprises configuring one or more controllable characteristics of at least one driving laser pulse of a high harmonic generation radiation source to control the output emission spectrum of illumination radiation provided by the high harmonic generation radiation source; and illuminating a target structure with said illuminating radiation. The method may comprise configuring the driving laser pulse so that the output emission spectrum comprises a plurality of discrete harmonic peaks. Alternatively the method may comprise using a plurality of driving laser pulses of different wavelengths such that the output emission spectrum is substantially monochromatic.

19 Claims, 6 Drawing Sheets

(51) Int. Cl.
*G02F 1/355* (2006.01)
*G02F 1/37* (2006.01)
*H01S 3/00* (2006.01)
*H01S 3/13* (2006.01)
*H01S 3/16* (2006.01)
*G01N 21/95* (2006.01)

(52) U.S. Cl.
CPC .............. *G02F 1/3551* (2013.01); *G02F 1/37* (2013.01); *G03F 7/70625* (2013.01); *G03F 7/70633* (2013.01); *H01S 3/0092* (2013.01); *H01S 3/1305* (2013.01); *H01S 3/1625* (2013.01); *H01S 3/1636* (2013.01)

(56) References Cited

U.S. PATENT DOCUMENTS

| | | | |
|---|---|---|---|
| 9,496,681 | B2 | 11/2016 | Vampa et al. |
| 2006/0066855 | A1 | 3/2006 | Boef et al. |
| 2011/0102753 | A1 | 5/2011 | Van De Kerkhof et al. |
| 2012/0044470 | A1 | 2/2012 | Smilde et al. |
| 2016/0149371 | A1* | 5/2016 | Vampa .................. H01S 5/042 372/22 |
| 2016/0315442 | A1 | 10/2016 | Popmintchev et al. |

FOREIGN PATENT DOCUMENTS

| | | |
|---|---|---|
| WO | WO 2017/025392 A1 | 2/2017 |
| WO | WO 2017/108410 A1 | 6/2017 |

OTHER PUBLICATIONS

Reitze et al., "Enhancement of high-order harmonic generation at tuned wavelengths through adaptive control," Optical Society of America, Optics Letters, vol. 29, No. 1, Jan. 1, 2004; pp. 86-88.

O'Keeffe et al., "Quasi-phase-matched high-order harmonic generation using tunable pulse trains," Optical Society of America, Optics Letters, vol. 22, No. 7, Apr. 7, 2014; pp. 7722-7732.

Brabec et al., "Intense few-cycle laser fields: Frontiers of nonlinear optics," The American Physical Society, Reviews of Modern Physics, vol. 72, No. 2, Apr. 2000; pp. 545-591.

Vozzi et al., "Generalized molecular orbital tomography," Nature Physics, vol. 7, Oct. 2011; pp. 822-826.

Shiner et al., "High harmonic cutoff energy scaling and laser intensity measurement with a 1.8 µm laser source," Journal of Modern Optics, vol. 60, No. 17, 2013; pp. 1458-1465.

Priori et al., "Nonadiabatic three-dimensional model of high-order harmonic generation in the few-optical-cycle regime," The American Physical Society, Physical Review A, vol. 61, No. 063801, 2000; pp. 1-8.

Sansone et al., "Nonadiabatic quantum path analysis of high-order harmonic generation: Role of the carrier-envelope phase on short and long paths," The American Physical Society, Physical Review A, vol. 70, No. 013411, 2004; pp. 1-10.

Ruchon et al., "Macroscopic effects in attosecond pulse generation," New Journal of Physics, vol. 10, No. 025027, 2008; pp. 1-10.

Mairesse et al., "Attosecond Synchronization of High-Harmonic Soft X-rays," Science, vol. 302, Nov. 28, 2003; pp. 1540-1543.

Zeng et al., "Tunable high-order harmonic generation and the role of the folded quantum path," The American Physical Society, Physical Review A, vol. 77, No. 023416, 2008; pp. 1-4.

Zhang et al., "Control of bandwidth and central wavelength of an enhanced extreme ultraviolet spectrum generated in shaped laser field," Optical Society of America, Optics Express, vol. 20, No. 15, Jul. 16, 2012; pp. 16544-16551.

Light Conversion Featured Products, Available at http://www.lightcon.com/products/product.php?ID=152, last updated 2016; 1 page.

International Search Report and Written Opinion of the International Searching Authority directed to International Application No. PCT/EP2017/058771, dated Jul. 26, 2017; 13 pages.

Anonymous, "Research Disclosure," Research Disclosure, Questel Ireland Ltd., R.D. Database No. 959023 (Nov. 2013); 8 pages.

Harada et al., "Development of standalone coherent EUV Scatterometry microscope with high-harmonic-generation EUV source," Proc. of SPIE vol. 8441 (2012); 10 pages.

Yeh et al., "Development of EUV scatterometer with high-harmonic-generation EUV source for nano-scale grating measurement," Proc. of SPIE vol. 9556 (2015); 8 pages.

\* cited by examiner

HHG SOURCE, INSPECTION APPARATUS AND METHOD FOR PERFORMING A MEASUREMENT

FIELD

The present invention relates to a HHG source, an inspection apparatus and a method for performing a measurement. In particular, it relates to an inspection apparatus comprised in a lithographic apparatus, as well as a method for performing a measurement therewith.

BACKGROUND

A lithographic apparatus is a machine that applies a desired pattern onto a substrate, usually onto a target portion of the substrate. A lithographic apparatus can be used, for example, in the manufacture of integrated circuits (ICs). In that instance, a patterning device, which is alternatively referred to as a mask or a reticle, may be used to generate a circuit pattern to be formed on an individual layer of the IC. This pattern can be transferred onto a target portion (e.g., including part of, one, or several dies) on a substrate (e.g., a silicon wafer). Multiple layers, each having a particular pattern and material composition, are applied to define functional devices and interconnections of the finished product.

In lithographic processes, it is desirable frequently to make measurements of the structures created, e.g., for process control and verification. Various tools for making such measurements are known, including scanning electron microscopes, which are often used to measure critical dimension (CD), and specialized tools to measure overlay, the accuracy of alignment of two layers in a device. Recently, various forms of scatterometers have been developed for use in the lithographic field.

Examples of known scatterometers often rely on provision of dedicated metrology targets. For example, a method may require a target in the form of a simple grating that is large enough that a measurement beam generates a spot that is smaller than the grating (i.e., the grating is underfilled). In so-called reconstruction methods, properties of the grating can be calculated by simulating interaction of scattered radiation with a mathematical model of the target structure. Parameters of the model are adjusted until the simulated interaction produces a diffraction pattern similar to that observed from the real target.

In addition to measurement of feature shapes by reconstruction, diffraction-based overlay can be measured using such apparatus, as described in published patent application US2006066855A1. Diffraction-based overlay metrology using dark-field imaging of the diffraction orders enables overlay measurements on smaller targets. These targets can be smaller than the illumination spot and may be surrounded by product structures on a wafer. Examples of dark field imaging metrology can be found in numerous published patent applications, such as for example US2011102753A1 and US20120044470A. Multiple gratings can be measured in one image, using a composite grating target. The known scatterometers tend to use light in the visible or near-IR wave range, which requires the pitch of the grating to be much coarser than the actual product structures whose properties are actually of interest. Such product features may be defined using deep ultraviolet (DUV) or extreme ultraviolet (EUV) radiation having far shorter wavelengths. Unfortunately, such wavelengths are not normally available or usable for metrology.

On the other hand, the dimensions of modern product structures are so small that they cannot be imaged by optical metrology techniques. Small features include for example those formed by multiple patterning processes, and/or pitch-multiplication. Hence, targets used for high-volume metrology often use features that are much larger than the products whose overlay errors or critical dimensions are the property of interest. The measurement results are only indirectly related to the dimensions of the real product structures, and may be inaccurate because the metrology target does not suffer the same distortions under optical projection in the lithographic apparatus, and/or different processing in other steps of the manufacturing process. While scanning electron microscopy (SEM) is able to resolve these modern product structures directly, SEM is much more time consuming than optical measurements. Moreover, electrons are not able to penetrate through thick process layers, which makes them less suitable for metrology applications. Other techniques, such as measuring electrical properties using contact pads is also known, but it provides only indirect evidence of the true product structure.

By decreasing the wavelength of the radiation used during metrology (i.e. moving towards the "soft X-ray" wavelength spectrum), the measurement performance improves since the radiation can resolve smaller structures or is more sensitive to structural variations of the structures. However, this requires a corresponding improvement in the spectral resolution of the metrology system. Additionally, the complexity of product structures is increasing, with product structures comprising increasing numbers of layers and a corresponding increase in thickness. This, in turn, increases the spectral resolution required to perform metrology measurements.

SUMMARY

In a first aspect of the invention, there is provided a method of performing a measurement in an inspection apparatus, comprising: configuring one or more controllable characteristics of at least one driving laser pulse of a high harmonic generation radiation source to control the output emission spectrum of illumination radiation provided by the high harmonic generation radiation source; and illuminating a target structure with said illuminating radiation The invention yet further provides an inspection apparatus comprising a high harmonic generation radiation source and operable to perform the method of the first aspect.

The invention yet further provides an inspection apparatus comprising a high harmonic generation radiation source, said high harmonic generation radiation source comprising a driving laser source operable to emit a driving laser pulse; wherein one or more controllable characteristics of the driving laser pulse is configured such that an output emission spectrum of the high harmonic generation radiation source comprises a plurality of discrete harmonic peaks.

The invention yet further provides an inspection apparatus comprising a high harmonic generation radiation source, said high harmonic generation radiation source comprising a plurality of driving laser sources, each being operable to emit a driving laser pulse with a different central wavelength.

The invention yet further provides a high harmonic generation radiation source comprising a plurality of driving laser sources, each being operable to emit a driving laser pulse with a different central wavelength.

The invention yet further provides a high harmonic generation radiation source comprising a driving laser source operable to emit a driving laser pulse; wherein one or more controllable characteristics of the driving laser pulse is configured such that an output emission spectrum of the high harmonic generation radiation source comprises a plurality of discrete harmonic peaks.

In the above it should be appreciated that "a plurality of driving laser sources" may comprise a plurality of separate laser devices, or (more typically) a single laser device with an output split into multiple beams, some or all of the multiple beams being conditioned in some manner (e.g., frequency converted by a frequency converter element) to change their wavelength. In this context, therefore, the sources may be the laser device itself and/or a frequency converter element, for example.

The invention yet further provides a computer program product containing one or more sequences of machine-readable instructions for implementing the configuring step in a method according to the first aspect.

Further aspects, features and advantages of the invention, as well as the structure and operation of various embodiments of the invention, are described in detail below with reference to the accompanying drawings. It is noted that the invention is not limited to the specific embodiments described herein. Such embodiments are presented herein for illustrative purposes only. Additional embodiments will be apparent to persons skilled in the relevant art(s) based on the teachings contained herein.

BRIEF DESCRIPTION OF THE DRAWINGS

Embodiments of the invention will now be described, by way of example only, with reference to the accompanying schematic drawings in which corresponding reference symbols indicate corresponding parts, and in which.

DETAILED DESCRIPTION OF EXEMPLARY EMBODIMENTS

Before describing embodiments of the invention in detail, it is instructive to present an example environment in which embodiments of the present invention may be implemented.

Figure 1:
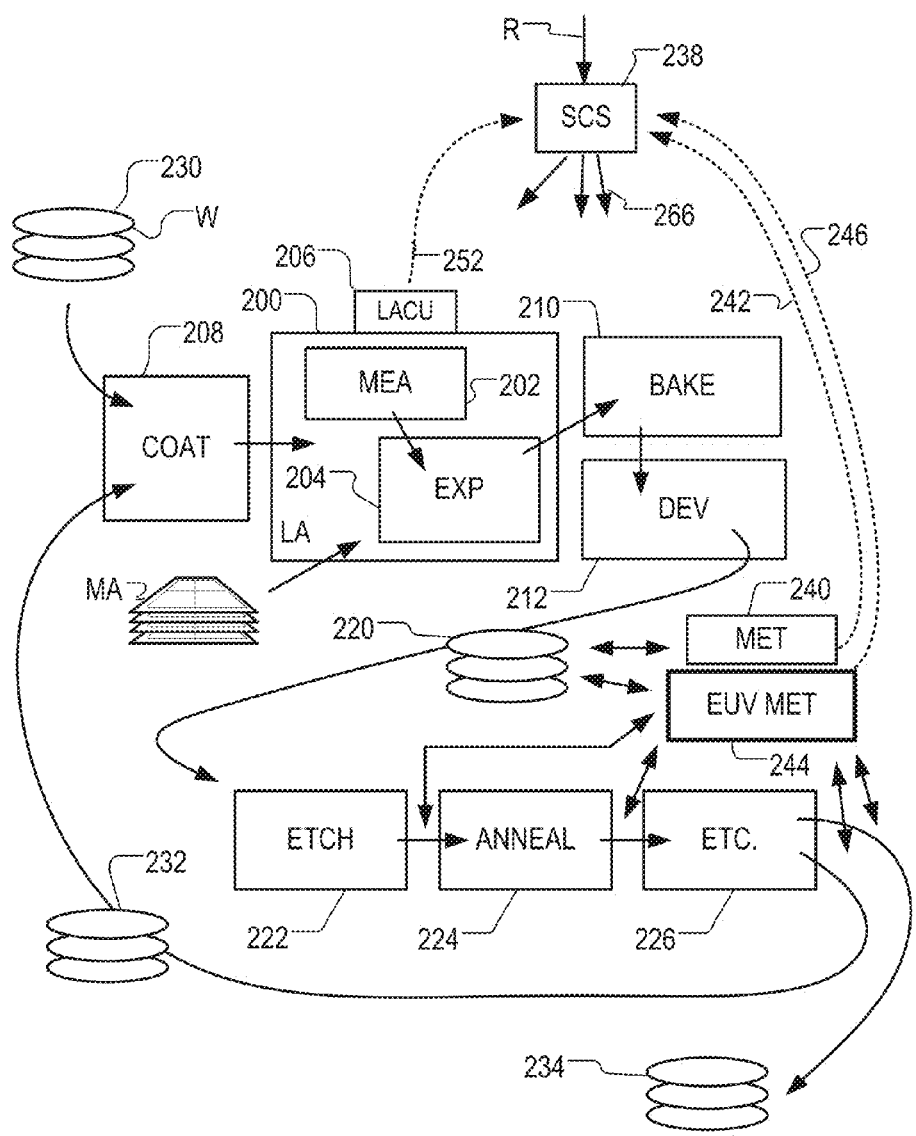
FIG. 1 depicts a lithographic apparatus together with other apparatuses forming a production facility for semiconductor devices.

FIG. 1 at 200 shows a lithographic apparatus LA as part of an industrial facility implementing a high-volume, lithographic manufacturing process. In the present example, the manufacturing process is adapted for the manufacture of for semiconductor products (integrated circuits) on substrates such as semiconductor wafers. The skilled person will appreciate that a wide variety of products can be manufactured by processing different types of substrates in variants of this process. The production of semiconductor products is used purely as an example which has great commercial significance today.

Within the lithographic apparatus (or "litho tool" 200 for short), a measurement station MEA is shown at 202 and an exposure station EXP is shown at 204. A control unit LACU is shown at 206. In this example, each substrate visits the measurement station and the exposure station to have a pattern applied. In an optical lithographic apparatus, for example, a projection system is used to transfer a product pattern from a patterning device MA onto the substrate using conditioned radiation and a projection system. This is done by forming an image of the pattern in a layer of radiation-sensitive resist material.

The term "projection system" used herein should be broadly interpreted as encompassing any type of projection system, including refractive, reflective, catadioptric, magnetic, electromagnetic and electrostatic optical systems, or any combination thereof, as appropriate for the exposure radiation being used, or for other factors such as the use of an immersion liquid or the use of a vacuum. The patterning MA device may be a mask or reticle, which imparts a pattern to a radiation beam transmitted or reflected by the patterning device. Well-known modes of operation include a stepping mode and a scanning mode. As is well known, the projection system may cooperate with support and positioning systems for the substrate and the patterning device in a variety of ways to apply a desired pattern to many target portions across a substrate. Programmable patterning devices may be used instead of reticles having a fixed pattern. The radiation for example may include electromagnetic radiation in the deep ultraviolet (DUV) or extreme ultraviolet (EUV) wavebands. The present disclosure is also applicable to other types of lithographic process, for example imprint lithography and direct writing lithography, for example by electron beam.

The lithographic apparatus control unit LACU which controls all the movements and measurements of various actuators and sensors to receive substrates W and reticles MA and to implement the patterning operations. LACU also includes signal processing and data processing capacity to implement desired calculations relevant to the operation of the apparatus. In practice, control unit LACU will be realized as a system of many sub-units, each handling the real-time data acquisition, processing and control of a sub-system or component within the apparatus.

Before the pattern is applied to a substrate at the exposure station EXP, the substrate is processed in at the measurement station MEA so that various preparatory steps may be carried out. The preparatory steps may include mapping the surface height of the substrate using a level sensor and measuring the position of alignment marks on the substrate using an alignment sensor. The alignment marks are arranged nominally in a regular grid pattern. However, due to inaccuracies in creating the marks and also due to deformations of the substrate that occur throughout its processing, the marks deviate from the ideal grid. Consequently, in addition to measuring position and orientation of the substrate, the alignment sensor in practice must measure in detail the positions of many marks across the substrate area, if the apparatus is to print product features at the correct locations with very high accuracy. The apparatus may be of a so-called dual stage type which has two substrate tables, each with a positioning system controlled by the control unit LACU. While one substrate on one substrate table is being exposed at the exposure station EXP, another substrate can be loaded onto the other substrate table at the measurement station MEA so that various preparatory steps may be carried out. The measurement of alignment marks is therefore very time-consuming and the provision of two substrate tables enables a substantial increase in the throughput of the apparatus. If the position sensor IF is not capable of measuring the position of the substrate table while it is at the measurement station as well as at the exposure station, a second position sensor may be provided to enable the positions of the substrate table to be tracked at both stations. Lithographic apparatus LA may for example is of a so-called dual stage type which has two substrate tables WTa and WTb and two stations—an exposure station and a measurement station—between which the substrate tables can be exchanged.

Within the production facility, apparatus 200 forms part of a "litho cell" or "litho cluster" that contains also a coating apparatus 208 for applying photosensitive resist and other coatings to substrates W for patterning by the apparatus 200. At an output side of apparatus 200, a baking apparatus 210 and developing apparatus 212 are provided for developing the exposed pattern into a physical resist pattern. Between all of these apparatuses, substrate handling systems take care of supporting the substrates and transferring them from one piece of apparatus to the next. These apparatuses, which are often collectively referred to as the track, are under the control of a track control unit which is itself controlled by a supervisory control system (SCS) 238, which also controls the lithographic apparatus via lithographic apparatus control unit LACU. Thus, the different apparatus can be operated to maximize throughput and processing efficiency. Supervisory control system SCS receives recipe information R which provides in great detail a definition of the steps to be performed to create each patterned substrate.

Once the pattern has been applied and developed in the litho cell, patterned substrates 220 are transferred to other processing apparatuses such as are illustrated at 222, 224, 226. A wide range of processing steps is implemented by various apparatuses in a typical manufacturing facility. For the sake of example, apparatus 222 in this embodiment is an etching station, and apparatus 224 performs a post-etch annealing step. Further physical and/or chemical processing steps are applied in further apparatuses, 226, etc. Numerous types of operation can be required to make a real device, such as deposition of material, modification of surface material characteristics (oxidation, doping, ion implantation etc.), chemical-mechanical polishing (CMP), and so forth. The apparatus 226 may, in practice, represent a series of different processing steps performed in one or more apparatuses.

As is well known, the manufacture of semiconductor devices involves many repetitions of such processing, to build up device structures with appropriate materials and patterns, layer-by-layer on the substrate. Accordingly, substrates 230 arriving at the litho cluster may be newly prepared substrates, or they may be substrates that have been processed previously in this cluster or in another apparatus entirely. Similarly, depending on the required processing, substrates 232 on leaving apparatus 226 may be returned for a subsequent patterning operation in the same litho cluster, they may be destined for patterning operations in a different cluster, or they may be finished products to be sent for dicing and packaging.

Each layer of the product structure requires a different set of process steps, and the apparatuses 226 used at each layer may be completely different in type. Further, even where the processing steps to be applied by the apparatus 226 are nominally the same, in a large facility, there may be several supposedly identical machines working in parallel to perform the step 226 on different substrates. Small differences in set-up or faults between these machines can mean that they influence different substrates in different ways. Even steps that are relatively common to each layer, such as etching (apparatus 222) may be implemented by several etching apparatuses that are nominally identical but working in parallel to maximize throughput. In practice, moreover, different layers require different etch processes, for example chemical etches, plasma etches, according to the details of the material to be etched, and special requirements such as, for example, anisotropic etching.

The previous and/or subsequent processes may be performed in other lithography apparatuses, as just mentioned, and may even be performed in different types of lithography apparatus. For example, some layers in the device manufacturing process which are very demanding in parameters such as resolution and overlay may be performed in a more advanced lithography tool than other layers that are less demanding. Therefore some layers may be exposed in an immersion type lithography tool, while others are exposed in a 'dry' tool. Some layers may be exposed in a tool working at DUV wavelengths, while others are exposed using EUV wavelength radiation.

In order that the substrates that are exposed by the lithographic apparatus are exposed correctly and consistently, it is desirable to inspect exposed substrates to measure properties such as overlay errors between subsequent layers, line thicknesses, critical dimensions (CD), etc. Accordingly a manufacturing facility in which litho cell LC is located also includes metrology system MET which receives some or all of the substrates W that have been processed in the litho cell. Metrology results are provided directly or indirectly to the supervisory control system SCS. If errors are detected, adjustments may be made to exposures of subsequent substrates, especially if the metrology can be done soon and fast enough that other substrates of the same batch are still to be exposed. Also, already exposed substrates may be stripped and reworked to improve yield, or discarded, thereby avoiding performing further processing on substrates that are known to be faulty. In a case where only some target portions of a substrate are faulty, further exposures can be performed only on those target portions which are good.

Also shown in FIG. 1 is a metrology apparatus 240 which is provided for making measurements of parameters of the products at desired stages in the manufacturing process. A common example of a metrology apparatus in a modern lithographic production facility is a scatterometer, for example an angle-resolved scatterometer or a spectroscopic scatterometer, and it may be applied to measure properties of the developed substrates at 220 prior to etching in the apparatus 222. Using metrology apparatus 240, it may be determined, for example, that important performance parameters such as overlay or critical dimension (CD) do not meet specified accuracy requirements in the developed resist. Prior to the etching step, the opportunity exists to strip the developed resist and reprocess the substrates 220 through the litho cluster. As is also well known, the metrology results 242 from the apparatus 240 can be used to maintain accurate performance of the patterning operations in the litho cluster, by supervisory control system SCS and/or control unit LACU 206 making small adjustments over time, thereby minimizing the risk of products being made out-of-specification, and requiring re-work. Of course, metrology apparatus 240 and/or other metrology apparatuses (not shown) can be applied to measure properties of the processed substrates 232, 234, and incoming substrates 230.

Each generation of lithographic manufacturing technology (commonly referred to as a technology "node") has tighter specifications for performance parameters such as CD. One of the main challenges in metrology is that the metrology target size is desired to be smaller than the targets customarily used with metrology apparatus 240. For example, a present goal is to use targets with a size of 5 μm×5 μm or smaller. These small sizes would permit wider use of so-called "in-die" metrology, where targets are located among the product structures (instead of being confined in scribe lane areas between product areas), or "on product" metrology, where the targets are the product structures themselves. The only metrology technique currently used for on-product CD metrology is electron microscopy (CD-SEM). This known technique shows limitations for future nodes, and only provides very limited geometrical information of the structure.

One approach to improving metrology of the smallest structures is to use shorter wavelengths of radiation, for example in the extreme ultraviolet (EUV), soft x-ray or even hard x-ray ranges. For example, EUV reflectometry, including spectroscopic EUV reflectometry, may be considered as a CD-metrology method for future technological nodes. X-ray scattering techniques such as small-angle x-ray scattering may also be considered, in transmissive mode (T-SAXS) or in grazing incidence mode (GI-SAXS). Principles and practice of EUV metrology in this context are provided in the patent application EP15160786, mentioned above. There it is demonstrated that EUV reflectometry offers benefits of high sensitivity, being robust against process variations and being selective for a parameter of interest.

For the purpose of the present disclosure, hard x-rays are considered as rays with wavelength less than about 0.1 nm, for example including the range 0.01 to 0.1 nm. Soft-x-ray or EUV refers to the range extending roughly from 0.1 nm to 125 nm wavelength. Different sub-ranges of these ranges can be chosen to suit the dimensions of structures under investigation. For example, for semiconductor structures at the limits of current lithographic techniques, wavelengths in the range 0.1 to 20 nm may be considered, or 0.1 to 10 nm, or 1 to 5 nm. Not only the size of structures, but also their material properties can influence the selection of wavelengths to use in investigations. For example, to perform reflectometry, at least background material of the structure requires good reflection strength at the wavelength used. For investigation of buried features, the wavelength should be chosen to obtain sufficient penetration through overlying material.

EUV metrology can be used to measure structures within the resist material treated within the litho cell (After Develop Inspection or ADI), and/or to measure structures after they have been formed in harder material (After Etch Inspection or AEI). For example, substrates may be inspected using EUV metrology apparatus 244 after they have been processed by the developing apparatus 212, etching apparatus 222, annealing apparatus 224 and/or other apparatus 226.

For high-volume manufacturing applications, a high brightness radiation source would be desirable, to reduce acquisition time for each measurement. The limited power of current compact x-ray sources means that known T-SAXS techniques suffer from a very low throughput, especially for small size metrology targets. This is especially the case when one seeks to obtain a very small spot size for illuminating a small target area on a substrate. Known EUV sources are also limited in brightness, and limited in selection of wavelengths. To maximize contrast in target structures and to discriminate between structures of different materials, fine control of the wavelength over a wide range would be desirable.

The manufacturing system illustrated in FIG. 1 includes one or more EUV metrology apparatuses 244 in addition to the optical scatterometer 240. This EUV metrology apparatus provides additional metrology results 246 which can be used by supervisory control system SCS to achieve further control of quality and improvement in performance of the lithographic manufacturing system as a whole. Like the optical scatterometer 240, metrology apparatus 244 can be applied at different stages in manufacture, such as ADI and AEI, mentioned above.

EUV Reflectometry Method

Figure 2:
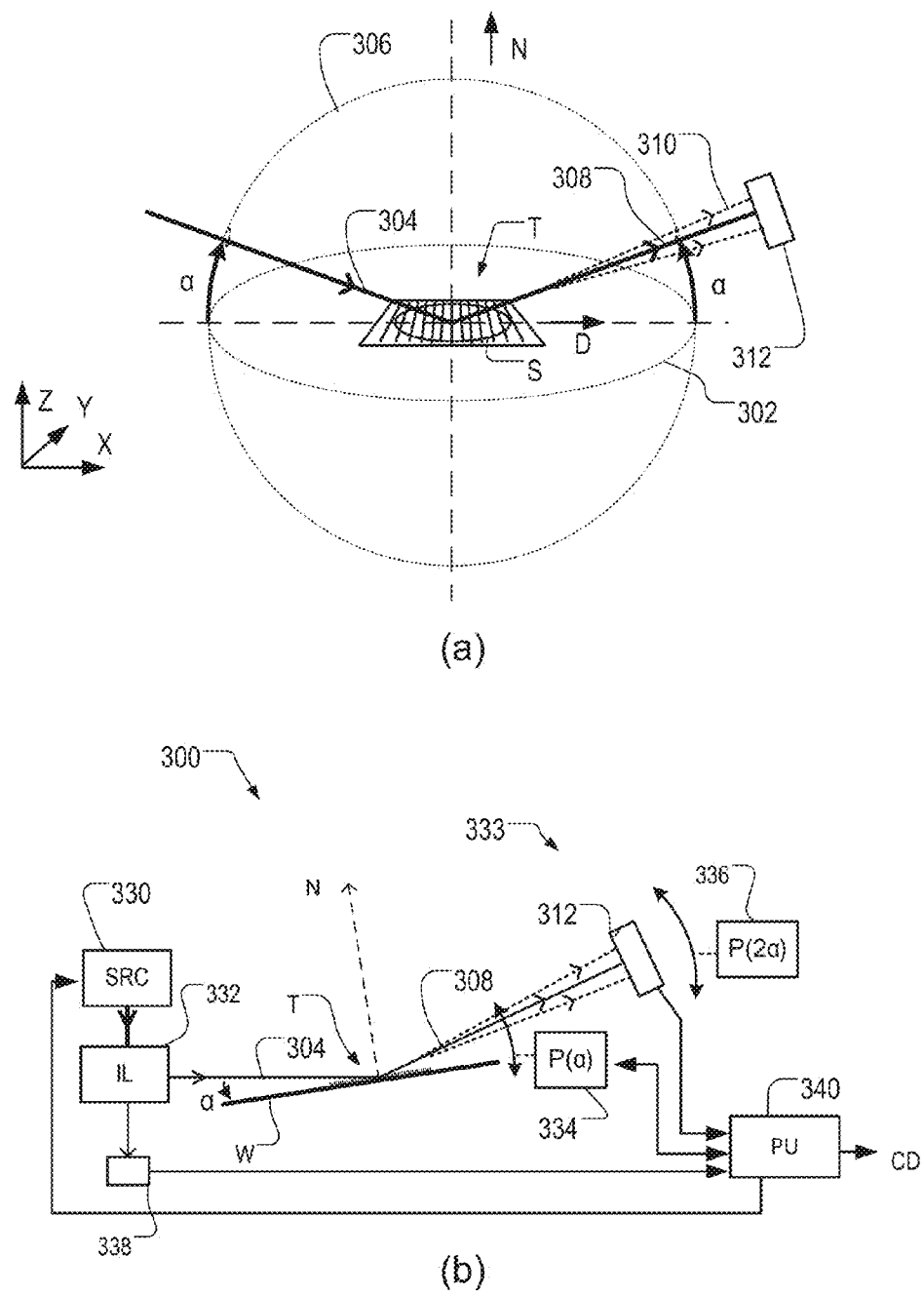
FIG. 2 illustrates (a) the geometry of incident and reflected rays in relation to a grating target in a metrology method according to a first embodiment of the present invention; and (b) illustrates schematically the components of a metrology apparatus, performing the method of FIG. 2(a)

FIG. 2 illustrates (a) a metrology method and (b) a metrology apparatus 300. The apparatus can be used as an example of EUV metrology apparatus 244 for measuring parameters of substrates W processed in the manufacturing system of FIG. 1. The apparatus can be used in wavebands other than EUV, In FIG. 2($a$), the target T is represented schematically as comprising a one-dimensional grating structure at the origin of a spherical reference frame. Axes X, Y and Z are defined relative to the target. (Of course any arbitrary coordinate system can be defined in principle, and each component may have its own local reference frame, that can be defined relative to the one shown.) The direction of periodicity D of the target structure is aligned with the X axis. The drawing is not a true perspective drawing, but a schematic illustration only. The X-Y plane is the plane of the target and substrate, and for clarity is shown tilted toward the viewer, represented by an oblique view of circle 302. The Z direction defines the direction N normal to the substrate. In FIG. 2($a$), a ray of incident radiation is labeled 304 and has an angle α of grazing incidence. In this example, the incident ray 304 (and all incident rays forming the radiation spot S) lie substantially in a plane parallel to the X-Z plane, that is a plane defined the directions D and N and represented by circle 306. A reflected ray 308 that is not scattered by the periodic structure of the target T (i.e. a ray of specular reflection) emerges towards the right hand side of the target in the diagram, with an elevation angle α.

Other rays 310 are scattered at angles different to the specular reflection, in accordance with diffraction properties of the target. The angle of separation between these rays and the specular ray will depend on the relationship between the wavelength of the radiation and the spacing of features of the target. The drawing is not to scale. For example, detector 312 may be closer to or further from the target than shown, the target grating will likely be very small relative to the detector; the angles of diffraction of rays 310 could be much wider than indicated.

To perform reflectometry, the ray 308 and/or the scattered rays 310 are captured by a photodetector 312. Detector 312 comprises for example a position-sensitive EUV detector, typically an array of detector elements. The array may be a linear array, but in practice a 2-dimensional array of elements (pixels) may be provided. Detector 313 may be for example a CCD (charge coupled device) image sensor or a CMOS image sensor. This detector is used to transform the reflected radiation into electrical signals and eventually digital data for analysis. A single pixel detector may be sufficient in principle for some types of measurement. More flexibility of operation will be allowed by having a two-dimensional image detector.

From the measured spectrum, obtained for one or more wavelengths and one or more values of incidence angle α, a measurement of a property of the target structure T can be calculated in a manner described further below.

EUV Reflectometry Apparatus

Turning to FIG. 2(b), metrology apparatus 300 is provided for measuring properties of a metrology target T formed on substrate W, by the method of FIG. 2(a). Various hardware components are represented schematically. The practical implementation of these components can be performed by the relevant skilled persons applying a mixture of existing components and specially-designed components, according to well-known design principles. A support (not shown in detail) is provided for holding the substrate at a desired position and orientation relative to other components to be described. A radiation source 330 provides radiation to an illumination system 332. Illumination system 332 provides a beam of radiation represented by ray 304 which (together with other rays forming an illuminating beam) forms a focused irradiation spot on target T. Detector 312 and any ancillary optical components may be conveniently considered as a detection system 333.

Substrate W in this example is mounted on a movable support having a positioning system 334 such that an angle of incidence a of ray 304 can be adjusted. In this example, it is chosen as a matter of convenience to tilt the substrate W to change the incidence angle, while the source 330 and illumination system 332 remain stationary. In order to catch the reflected ray 308, detection system 333 is provided with a further movable support 336, so that it moves through an angle 2a relative to the stationary illumination system, or through an angle α relative to the substrate. In the grazing incidence regime of reflectometry, it is convenient to define the incidence angle α by reference to the plane of the substrate, as shown. Of course, it could equally be defined as an angle between the direction of incidence of incident ray 304 and a direction N normal to the substrate.

In alternative embodiments, the angle of incidence can be varied in more than one dimension, for example by use of a conical mount. This type of arrangement and its potential benefits are described in detail in the European patent application number 15160786, mentioned above. The entire contents of that application are incorporated herein by reference.

Additional actuators, not shown, are provided for bringing each target T into a position where the focused spot S of radiation is located. (Looking at it another way, to bring the spot to the position where the target is located.) In a practical application, there may be a succession of individual targets or target locations to be measured on a single substrate, and a succession of substrates too. It is immaterial, in principle, whether the substrate and target are moved and reoriented while the illumination system and detector stay still, or whether the substrate stays still while the illumination system and detector are moved, or whether different components of the relative movement are achieved by a combination of these techniques. The present disclosure encompasses all these variants.

As already described with reference to FIG. 2(a), the radiation reflected by target T and substrate W is split into a spectrum 310 of rays of different wavelengths, before it impinges on detector 312. A second detector 338 will normally also be provided for measuring intensity of the incident beam, for use as a reference. A processor 340 receives signals from the detectors 312 and 338. The resulting reflection data for one or more angles of incidence are used in the processor to calculate a measurement of property of the target, for example CD or overlay.

FIG. 3(a) shows schematically the key elements of an inspection apparatus implementing so-called dark field imaging metrology, and in particular in the context of overlay metrology. The apparatus may be a stand-alone device or incorporated in either the lithographic apparatus 200, e.g., at the measurement station 202, or the metrology station 240, 244. An optical axis, which has several branches throughout the apparatus, is represented by a dotted line O. A target grating structure T and diffracted rays are illustrated in more detail in FIG. 3(b).

As described in the prior applications cited in the introduction, the dark-field-imaging apparatus of FIG. 3(a) may be part of a multi-purpose angle-resolved scatterometer that may be used instead of or in addition to a spectroscopic scatterometer. In this type of inspection apparatus, radiation emitted by a radiation source 11 is conditioned by an illumination system 12. For example, illumination system 12 may include a collimating lens system and an aperture device. The conditioned radiation follows an illumination path, in which it is reflected by partially reflecting surface 15 and focused into a spot S on substrate W via a microscope objective lens 16. A metrology target T may be formed on substrate W. Lens 16, has a high numerical aperture (NA), preferably at least 0.9 and more preferably at least 0.95. Immersion fluid can be used to obtain with numerical apertures over 1 if desired. The multi-purpose scatterometer may have two or more measurement branches. Additionally, further optical systems and branches will be included in a practical apparatus, for example to collect reference radiation for intensity normalization, for coarse imaging of capture targets, for focusing and so forth. Details of these can be found in the prior publications mentioned above. For the purposes of the present disclosure, only the measurement branch of interest for the dark-filed imaging metrology is illustrated and described in detail.

In the collection path for dark-field imaging, imaging optical system 21 forms an image of the target on the substrate W on sensor 23 (e.g. a CCD or CMOS sensor). An aperture stop 20 is provided in a plane P' in the collection path. Plane P' is a plane conjugate to a pupil plane P (not shown) of objective lens 16. Aperture stop 20 may also be called a pupil stop. Aperture stop 20 can take different forms, just as the illumination aperture can take different forms. The aperture stop 20, in combination with the effective aperture of lens 16, determines what portion of the scattered radiation is used to produce the image on sensor 23. Typically, aperture stop 20 functions to block the zeroth order diffracted beam so that the image of the target formed on sensor 23 is formed only from the first order beam(s). In an example where both first order beams are combined to form an image, this would be the so-called dark field image, equivalent to dark-field microscopy. In the present application, however, only one of the first orders is imaged at a time, as explained below. The images captured by sensor 23 are output to image processor and controller 40, the function of which will depend on the particular type of measurements being performed. For the present purpose, measurements of asymmetry of the target structure are performed. Asymmetry measurements can be combined with knowledge of the target structures to obtain measurements of performance parameters of lithographic process used to form them. Performance parameters that can be measured in this way include for example overlay, focus and dose.

Where a metrology target T is provided on substrate W, this may be a 1-D grating, which is printed such that after development, the bars are formed of solid resist lines. The target may be a 2-D grating, which is printed such that after development, the grating is formed of solid resist pillars or vias in the resist. The bars, pillars or vias may alternatively be etched into the substrate. Each of these gratings is an example of a target structure whose properties may be investigated using the inspection apparatus.

The various components of illumination system 12 can be adjustable to implement different metrology 'recipes' within the same apparatus. In addition to selecting wavelength (color) and polarization as characteristics of the particular, illumination system 12 can be adjusted to implement different illumination profiles. Because plane P" is conjugate with pupil plane P of objective lens 16 and the plane of the detector 19, an illumination profile in plane P" defines the angular distribution of light incident on substrate W in spot S. To implement different illumination profiles, an aperture device can be provided in the illumination path. The aperture device may comprise different apertures mounted on a movable slide or wheel. It may alternatively comprise a programmable spatial light modulator. As a further alternative, optical fibers may be disposed at different location in the plane P" and used selectively to deliver light or not deliver light at their respective locations. These variants are all discussed and exemplified in the documents cited above.

In a first example illumination mode, rays 30a are provided so that the angle of incidence is as shown at 'I' and the path of the zero order ray reflected by target T is labeled '0' (not to be confused with optical axis 'O'). In a second illumination mode, rays 30b can be provided, in which case the angles of incidence and reflection will be swapped. Both of these illumination modes will be recognized as off-axis illumination modes. Many different illumination modes can be implemented for different purposes.

As shown in more detail in FIG. 3(b), target grating T as an example of a target structure is placed with substrate W normal to the optical axis O of objective lens 16. In the case of an off-axis illumination profile, a ray of illumination I impinging on grating T from an angle off the axis O gives rise to a zeroth order ray (solid line 0) and two first order rays (dot-chain line +1 and double dot-chain line −1). It should be remembered that with an overfilled small target grating, these rays are just one of many parallel rays covering the area of the substrate including metrology target grating T and other features. Since the beam of illuminating rays 30a has a finite width (necessary to admit a useful quantity of light), the incident rays I will in fact occupy a range of angles, and the diffracted rays 0 and +1/−1 will be spread out somewhat. According to the point spread function of a small target, each order +1 and −1 will be further spread over a range of angles, not a single ideal ray as shown.

Referring also to FIG. 3(a), under the first illumination mode with rays 30a, +1 order diffracted rays from the target grating will enter the objective lens 16 and contribute to the image recorded at sensor 23. When the second illumination mode is used, rays 30b are incident at an angle opposite to rays 30b, and so the −1 order diffracted rays enter the objective and contribute to the image. Aperture stop 20 blocks the zeroth order radiation when using off-axis illumination. As described in the prior publications, illumination modes can be defined with off-axis illumination in X and Y directions.

By comparing images of the target grating under these different illumination modes, asymmetry measurements can be obtained. Alternatively, asymmetry measurements could be obtained by keeping the same illumination mode, but rotating the target. While off-axis illumination is shown, on-axis illumination of the targets may instead be used and a modified, off-axis aperture 20 could be used to pass substantially only one first order of diffracted light to the sensor. In a further example, prisms are used in place of aperture stop 20 which have the effect of diverting the +1 and −1 orders to different locations on sensor 23 so that they can be detected and compared without the need for two sequential image capture steps. This technique, is disclosed in the above-mentioned published patent application US2011102753A1, the contents of which are hereby incorporated by reference. 2nd, 3rd and higher order beams (not shown in FIG. 3) can be used in measurements, instead of or in addition to the first order beams. As a further variation, the off-axis illumination mode can be kept constant, while the target itself is rotated 180 degrees beneath objective lens 16 to capture images using the opposite diffraction orders.

Some scatterometry techniques are typically performed using radiation with a visible wavelength. As such, the scatterometry targets (or at least those for which higher order diffraction measurements are made) have a pitch that is larger than that of the product structures on the substrate. As an example, a scatterometry target may have a target grating pitch measured in microns (μm), whereas product structures on the same substrate may have a pitch measured in nanometers (nm).

This difference in pitch induces an offset between the measured overlay and the actual overlay on the product structures. The offset is at least partly due to optical projection distortions in the lithographic apparatus and/or different processing in other steps of the manufacturing process. Presently, the offset comprises a significant contribution to the overall measured overlay. Reducing or eliminating it will therefore improve overall overlay performance.

In order to perform diffraction-based measurements on structures with a pitch corresponding to that of a product structure, it is necessary to use radiation with a shorter wavelength than visible light. However, a number of materials, such as polycrystalline silicon or amorphous carbon, which are presently used in many layers of product structures absorb ultraviolet radiation. It has, however, been found that absorption losses for radiation in the "soft X-ray" spectrum (approximately 2 nm-40 nm) is much lower than for ultraviolet radiation. It should of course be noted that the specific absorbance of a product structure is dependent on the specific materials used in the layers. Given knowledge of the properties of the materials used in a particular structure, it is possible to select the radiation wavelength used so as to minimize absorption losses.

In order to maximize the accuracy of a diffraction-based measurement, e.g. to determine overlay error, it is necessary to optimize the properties of the radiation that arrives at the detector. The property of the scattered radiation is dependent the properties of the radiation used and the properties of the structure under measurement. One parameter that may be used to describe the quality of the scattered radiation is the so-called "stack sensitivity". This parameter describes the strength of the measured asymmetry caused by an upper target grating shifting relative to a lower target grating. It has been found that the "stack sensitivity" varies periodically in dependence on the wavelength of the radiation and the thickness of the target structure. The period of the variation $\Delta\lambda_s$, which determines the resolution for a stack thickness T, can be described as:

$$\Delta\lambda_s = \frac{\lambda^2}{2T} \quad (1)$$

where $\lambda$ is the wavelength of the radiation, and T is the optical thickness of the structure being measured. An exemplary optical thickness of a product structure may be 400 nm, and an exemplary radiation wavelength may be $\lambda=13$ nm. In this example, the period of the "stack sensitivity" variation $\Delta\lambda_s$ is 0.21 nm.

In order to optimize the radiation measured at the detector, it is necessary for the inspection apparatus to have a spectral resolution that is better than the size of the periodic variations of the stack sensitivity $\Delta\lambda_s$. Specifically, in order to fully resolve the periodic variations of the stack sensitivity, the required spectral resolution $\Delta\lambda_r$ of the inspection apparatus should be at least double that of the variation period $\Delta\lambda_s$. In the present example, therefore, the required spectral resolution $\Delta\lambda_r$ for the inspection apparatus may be approximately 0.1 nm.

Figure 3:
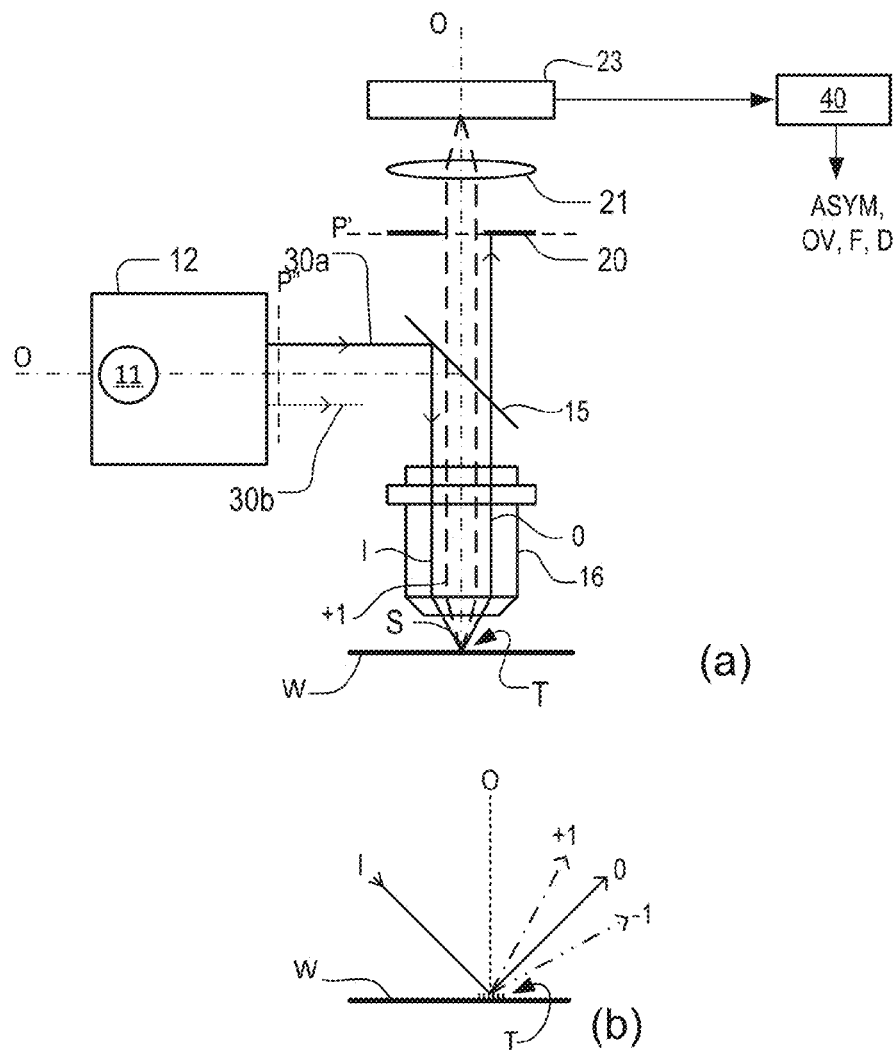
FIG. 3 illustrates (a)-(b) schematically an inspection apparatus adapted to perform a method according to an embodiment of the present invention.

The spectral resolution of an inspection apparatus, such as the one illustrated in FIG. 2(b) or FIG. 3, is determined by the properties of the optical system and the properties of the target structure. Due to target size constraints, the spot diameter of a typical inspection apparatus is limited to approximately 2 μm. Assuming that the illuminating radiation is a Gaussian beam, the following relation between the beam waist diameter D and the numerical aperture of the illuminating radiation NA (half angle) can be derived:

$$D = \frac{2}{\pi} \frac{\lambda}{NA} \quad (2)$$

For illuminating radiation with a wavelength of $\lambda=13$ nm, the numerical aperture can be derived as NA=4 mrad.

Presently, the pitch of product structures is approximately P=40 nm. The spectral resolution of a diffraction-based inspection apparatus (e.g. a scatterometer) measuring a target structure with this pitch (i.e., the grating resolution) $\Delta\lambda_g$ (assuming $\lambda\ll$pitch size) can be derived as:

$$\Delta\lambda_g \approx 2\times P\times NA = 80\times 0.004 = 0.32 \text{ nm}. \quad (3)$$

The grating resolution $\Delta\lambda_g$ is larger than the required spectral resolution $\Delta\lambda_r$ of 0.1 nm. In other terms, it is not possible to adequately resolve the periodic variations of the stack sensitivity. It is possible to improve the grating resolution $\Delta\lambda_g$ by reducing the size of the numerical aperture. However, this will in turn require the target size to be increased. This is because a decrease in NA will result in a larger spot diameter. As discussed above, targets must be "underfilled" (i.e. the spot diameter is smaller than the size of the target). If the spot diameter is increased, the size of the target must therefore also be increased proportionally. Larger targets take up more space on the surface of a substrate, which is undesirable in a production environment since it increases the per-product manufacturing costs. In the following, a method and apparatus that improves the spectral resolution of the inspection apparatus will be described.

A HHG (High Harmonic Generation) source is preferred for generation of the wavelengths required for measurement of product-resolution pitches, because of its high brightness. Such a HHG source enables a small focused spot on a diffraction based overlay (DBO) target at a high photon flux. The output of HHG, however, is not a single spectral line; instead it may contain discrete harmonic orders or be a super-continuum of soft x-ray wavelengths. The accuracy of such DBO techniques depend on a good spectrally resolved measurement, i.e. $\Delta\lambda_g \leq \Delta\lambda_r < \Delta\lambda_s$. A monochromator could be used but this is very lossy in the soft X-ray domain. Moreover, it would add volume and limit the flexibility of the measurement set-up.

Figure 4:
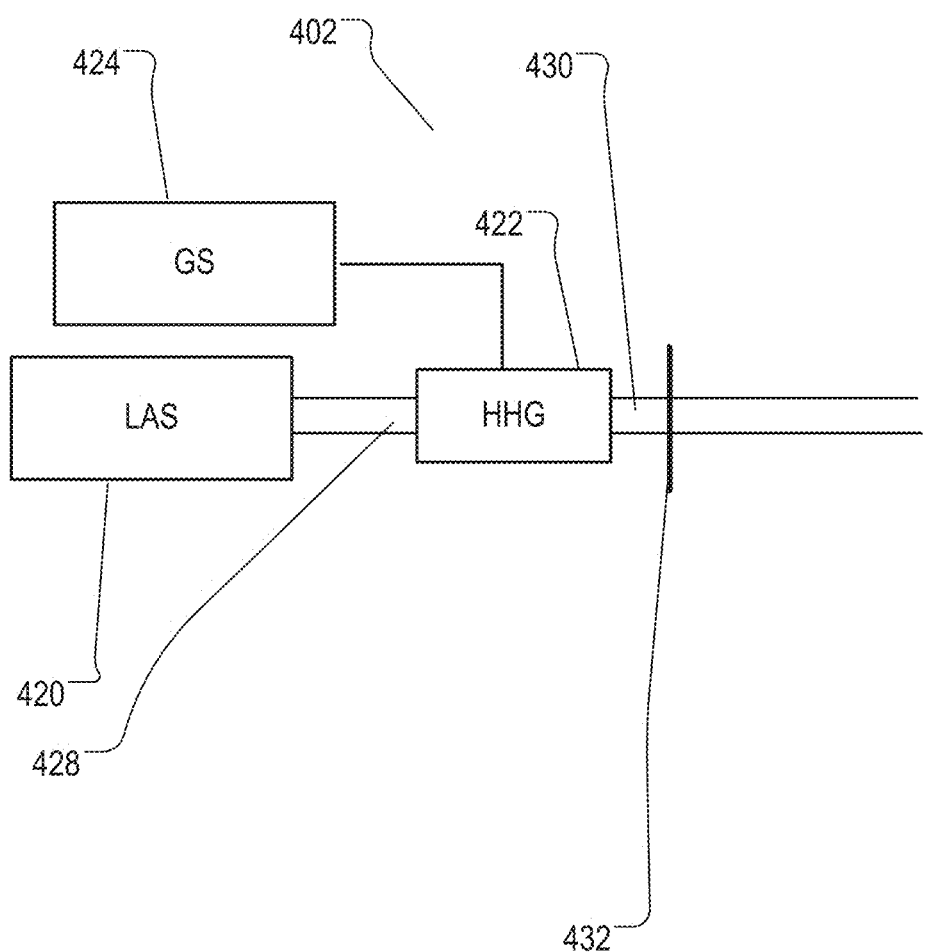
FIG. 4 shows schematically the construction of a radiation source used in the apparatus of FIG. 2(b) or FIG. 3.

FIG. 4 shows a source 402 comprising for example a generator of EUV radiation based on high harmonic generation (HHG) techniques. Main components of the radiation source are a pump laser 420 and an HHG gas cell 422. A gas supply 424 supplies suitable gas to the gas cell. The pump laser may be for example a Ti:Saph based laser, producing pulses in the sub-picosecond range with a several kHz repetition rate, having a wavelength of 800 nm. Alternatively the pump laser may be a fiber-based laser with an optical amplifier, with a pulse repetition rate up to several megahertz, as required. Typical pulse durations may be in the sub-picosecond range. The wavelength may be for example in the region of 1 μm. The laser pulses are delivered as a first beam of radiation 428 to the HHG gas cell 422, where a portion of the radiation is converted to higher frequencies. The output radiation beam 430 includes coherent radiation of the desired EUV wavelength or wavelengths. One or more filtering devices 432 may be provided. For example a filter such as a thin membrane of Aluminum (Al) may serve to cut the fundamental IR radiation from passing further into the inspection apparatus. Some or all of the radiation path may be contained within a vacuum environment, bearing in mind that the desired EUV radiation is absorbed when traveling in air. The various components of radiation source 402 and illumination optics 404 can be adjustable to implement different metrology 'recipes' within the same apparatus. For example different wavelengths and/or polarizations can be made selectable.

It is proposed to configure the HHG emission spectrum so as to optimize the spectral resolution and/or to maximize output at a particular wavelength. In a first embodiment, it is proposed to configure one or more controllable characteristics of the driving laser pulse of the HHG to obtain a HHG emission spectrum comprising narrow bandwidth harmonic peaks, wherein one or more of the harmonic peaks has a bandwidth meeting the spectral resolution requirement described above. As such this bandwidth (e.g., as measured full-width-half-maximum) may be smaller than 0.2 nm, smaller than 0.15 nm or smaller than 0.12 nm. In an embodiment this bandwidth may be in the region of 0.1 nm. The driving pulse may also be configured such that the separation of adjacent harmonic peaks is sufficiently large as to overcome the spectrum blur due to the requirement of a small NA and grating pitch, as described by Equation (3).

Figure 5:
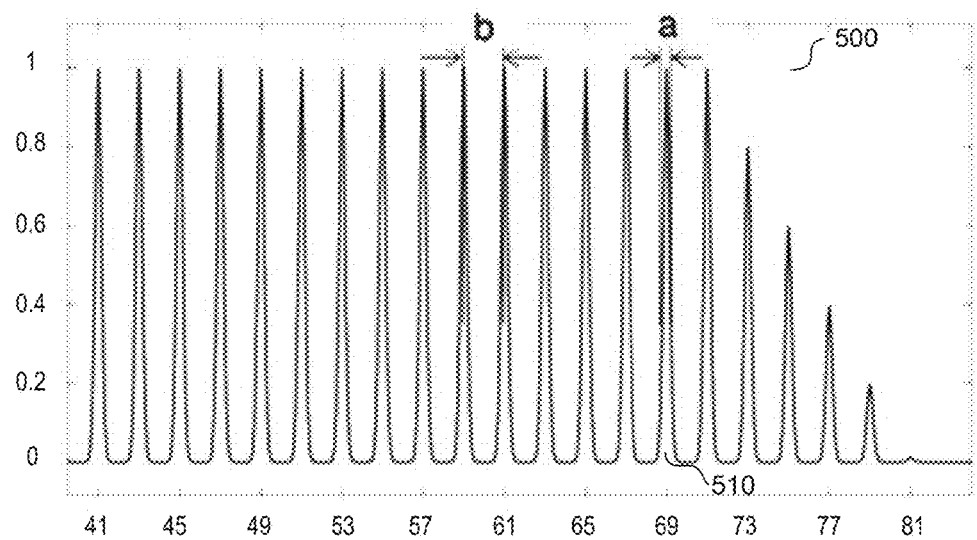
FIG. 5 is a graph of intensity (y-axis) against energy (x-axis) showing an emission spectrum of a HHG source of an embodiment of the invention.

FIG. 5 shows a schematic HHG emission spectrum 500 with intensity on the y-axis against energy (harmonic order) on the x-axis. The bandwidth (labelled a on FIG. 5) of a single harmonic 510 is generally related to the spectral bandwidth of the driving laser. The smaller the spectral bandwidth of this driving laser (i.e., the longer, temporally, the laser driving pulse), the narrower each harmonic peak will be. This is because a typical driving laser field comprises multi-cycle oscillations and each cycle can produce harmonic generations. The final HHG emission spectrum is a coherent superposition of all the generations. The more cycles to average, the sharper the harmonic will be.

Figure 6:
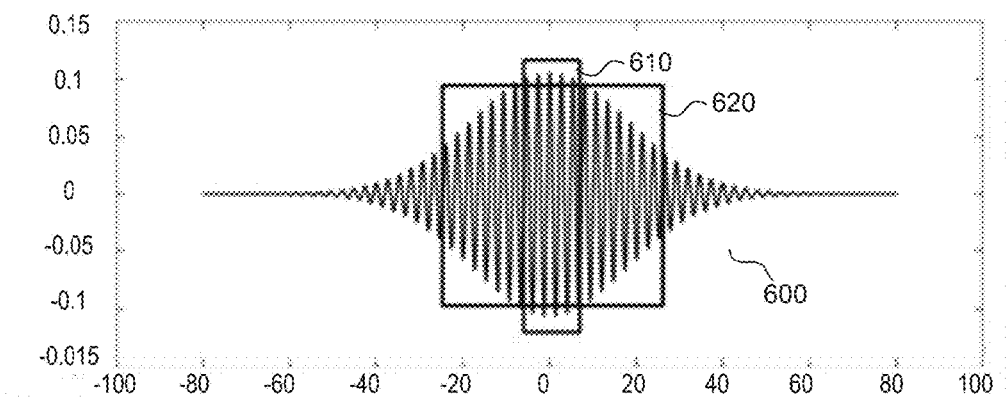
FIG. 6 is a graph of intensity (y-axis) against time (x-axis) showing a laser driving pulse of a HHG source of an embodiment of the invention.

FIG. 6 shows a laser driving pulse 600 as a plot of intensity (a.u.) on the y-axis against time (fs) on the x-axis. Within the laser driving pulse 600, there are only a relatively few cycles (i.e., those cycles within rectangle 610) which can produce HHG in the cut-off region of the emission spectrum 500 (the orders with relatively high photon energy, e.g., those between orders 71 and 81). The bandwidths for these harmonics are therefore relatively broad due to the lower average intensity. However, the harmonics in the plateau region of the HHG spectrum 500, with relatively low photon energy, are generated by a large number of cycles (i.e., those cycles within square 620) and as a consequence normally have very sharp spectral linewidths.

Therefore it is proposed to obtain sharp harmonic peaks (and therefore high spectral resolution) by using a relatively long laser driving pulse and selecting a harmonic in the plateau region of the HHG spectrum 500. "Selecting" in this context may comprise using the generated harmonic for a particular measurement. This may comprise configuring the system such that the required diffraction orders from the selected harmonic fall on the detector and the measurements made from this harmonic. However, there is an effective limit on the laser driving pulse duration. The peak intensity is required to be sufficiently high to enter the tunnel ionization regime. Furthermore, a pulse of too greater duration may cause ionization depletion of the ground state such that there is no electron remaining for HHG. It is therefore proposed that the laser driving pulse comprise between 10 and 30 cycles (and therefore be of approximately 25-75 fs duration) or between 15 and 30 cycles (approximately 37-75 fs duration). In more specific embodiments, the laser driving pulse may comprise between 15 and 25 cycles (approximately 37-63 fs duration), or between 17 and 22 cycles (approximately 43-55 fs duration), or in the region of 19 or 20 cycles (approximately 50 fs duration).

The spectral interval (labelled b on FIG. 5) between adjacent harmonic orders $\Delta\lambda_h$ is given by:

$$\Delta\lambda_h = \frac{\lambda_D}{N} - \frac{\lambda_D}{N+2} \approx \frac{2\lambda_D}{N^2} = \frac{2\lambda^2}{\lambda_D} \quad (4)$$

where $\lambda_D$ is the wavelength of the laser driving pulse, and $\lambda$, is the (EUV) wavelength corresponding to harmonic N (only odd harmonics are present). Note that this spectral interval $\Delta\lambda_h$ scales with $\lambda^2$, similarly to the variation period $\Delta\lambda_s$ of Equation (1).

Another controllable characteristic of the laser driving pulse is its central wavelength. The spectral position of the HHG emission spectrum varies with this laser driving pulse central wavelength, and therefore the position of a particular harmonic can be tuned spectrally by appropriate tuning of the laser driving pulse central wavelength. This can be utilised to optimize measurement sensitivity, as measurement sensitivity is a function of the measurement radiation wavelength. In an embodiment, this comprises tuning the laser driving pulse central wavelength such that a chosen harmonic (e.g., a harmonic in the plateau region of the emission spectrum) has a peak intensity corresponding to a desired wavelength, for example a wavelength of maximum sensitivity for a measurement.

Figure 7:
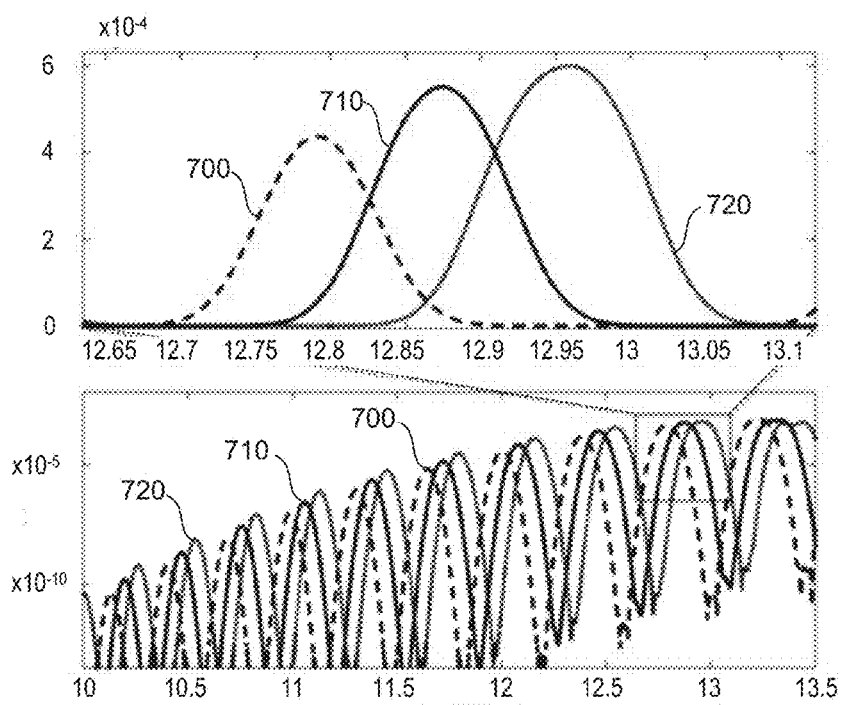
FIG. 7 is a graph of intensity (y-axis) against energy (x-axis) showing emission spectra of a HHG source driven by a laser with three different central driving wavelengths.

FIG. 7 are graphs of intensity (y-axis) against output wavelength (x-axis) showing a first emission spectrum 700 (dashed line) corresponding to a first laser driving pulse central wavelength (e.g., 790 nm), a second emission spectrum 710 (solid line) corresponding to a second laser driving pulse central wavelength (e.g., 795 nm) and a third emission spectrum 720 (dotted line) corresponding to a third laser driving pulse central wavelength (e.g., 800 nm). The bottom graph show the spectra over a range of wavelengths on the x-axis against intensity (log scale) on the y-axis. The top graph shows a detail of the bottom graph in the region of a single corresponding harmonic of each of the spectra (note the linear scale on the y-axis which makes the peaks look broader in the top graph). It can be seen that the wavelength of this single harmonic can be varied (in this specific example between approximately 12.79 nm and 12.96 nm) by appropriate control of the laser driving pulse central wavelength.

Other systems, such as optical parameter amplification (OPA) systems, may enable further tuning possibilities as such systems (e.g., with second harmonic generation) enable a broad tuning range for the laser driving pulse central wavelength; for example, a tuning range of between 580 nm and 2600 nm.

It can be further observed from FIG. 7, that the bandwidth for each of the harmonic peaks is approximately 0.1 nm, for a laser driving pulse of approximately 50 fs (19-20 cycles) which is smaller than the desired spectral resolution for the overlay sensitivity according to Equation (1).

As an alternative to increasing spectral resolution of a multiple wavelength HHG source output, another embodiment proposes providing a tunable monochromatic HHG output. A monochromatic source will make a measurement simpler in practice. In an embodiment it is proposed to tune the monochromatic HHG emission such that it corresponds to the maximum overlay and/or CD sensitivity for a target. A monochromator could be used for this, but it would be very lossy in the soft x-ray domain. Moreover, it adds volume and limits the flexibility of the measurement set-up. Here, an optical way to gate out the required spectral region of the HHG emission is described. The tunable feature of this technique can also be used to increase the grating resolution by bringing the output wavelength closer to the target pitch size. According to the first order grating equation for a normal incidence radiation, the diffraction angle θ is given by:

$$\theta = \arcsin\left(\frac{\lambda}{p}\right) \quad (5)$$

where the p is the grating pitch size (e.g., p=40 nm) and λ is the emission wavelength.

Figure 8:
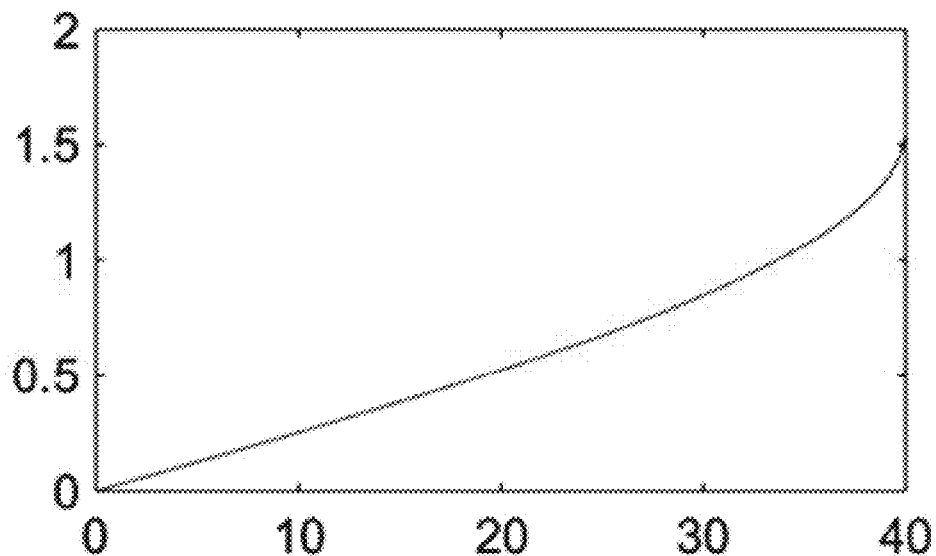
FIG. 8 is a graph of first order diffraction angle (y-axis) against wavelength (x-axis) for normal incidence radiation on a grating with pitch of 40 nm, illustrating the effect of wavelength on dispersion.

FIG. 8 is a graph illustrating the relation between diffraction angle θ (y-axis) and wavelength λ, (x-axis) for a grating of pitch p=40 nm. As can be seen, the dispersion is significantly bigger for a wavelength close to the pitch size p compared to that of the smaller wavelength. Equation (3), describing the relation between grating resolution $\Delta\lambda_g$, NA and pitch, is basically the linearization of Equation (5) in the limit that $\lambda \ll p$, and then applied to the full opening angle of the beam 2NA. If a small wavelength limit is not assumed, the relation is given by:

$$\Delta\lambda_g = 2NA\sqrt{p^2 - \lambda^2} \quad (6)$$

It is now clear that making wavelength λ close to pitch p leads to the optimal resolution $\Delta\lambda_g$. For example, evaluating this equation for a wavelength λ around 13 nm and an NA of 0.004 gives a grating resolution $\Delta\lambda_g$=0.3 nm, which is larger than the required resolution $\Delta\lambda_r$=0.1 nm. Therefore, this dispersion is not sufficient for resolving the fast oscillation in the stack sensitivity. However, if the wavelength of HHG is tuned to a wavelength λ around 38 nm, a grating resolution of $\Delta\lambda_g=0.1$ nm is obtained, and this will be sufficient to resolve the fast oscillation in the stack sensitivity. Note that the required resolution $\Delta\lambda_r$ can also be increased when the wavelength increases, as Equation (1) also scales with wavelength, hence wavelengths shorter than 38 nm will already provide sufficient resolution.

It is proposed to temporally shape the total electric driving field in a way such that the HHG emission spectrum is enhanced in a narrow wavelength band, but is suppressed elsewhere. This is can be done by combining multiple laser fields, each having a different central wavelength. Such a concept is described in the paper "Control of bandwidth and central wavelength of an enhanced extreme ultraviolet spectrum generated in shaped laser field", Zhang C. et al; Optics Express Vol. 20, No. 15. In a specific non-limiting example, it is proposed to use 400 nm (second harmonic generation SHG), 800 nm and 2000 nm (OPA) driving laser pulses to generate each field. Compared to the techniques taught in Zhang, these wavelengths have been determined to be more practical, as two OPAs are not required. The 400 nm pulse may be obtained by frequency doubling of the 800 nm direct laser output (e.g., using a frequency converter element such as a β-Barium borate (BBO) crystal). In such an embodiment, only the 2000 nm pulse is obtained using an OPA.

It is proposed to optimize the HHG emission spectrum by tuning one or more controllable characteristics of each of the different wavelength driving laser pulses, to achieve a narrow emission spectrum (e.g., such that only a single harmonic is preferred and a near monochromatic output obtained). In this context, a near monochromatic output may comprise an output where the intensity of the peak harmonic emission is at least one order of magnitude greater than the other harmonic emissions of the HHG emission spectrum. The controllable characteristics may comprise one or more of intensity, pulse duration and/or carrier-envelope phase (CEP). Once this optimization has been performed, the intensity ratio between one of the driving laser pulses and one or both of the other driving laser pulses can be varied to select the actual spectral region output (e.g., the output peak wavelength). In a specific embodiment, it may be the intensity ratio between the 2000 nm driving laser pulse relative to the sum of the 400 nm and 800 nm driving laser pulses which is varied to vary the driving field and therefore to select the emission spectral region.

The proposed method can be used to tune the peak HHG harmonic emission (e.g., having an intensity at least one order of magnitude greater than the other harmonic emissions of the HHG emission spectrum) in a wide spectral range from <10 nm (e.g., 2 nm) to 40 nm; or between 10 nm to 15 nm.

Tunable HHG sources, such as described herein, provide much freedom in EUV-overlay and CD measurement. Depending on the different targets having different stack thickness, reflectivity, pitch size, it is possible to freely shape the EUV radiation source to optimize the EUV-overlay performance. The choice of wavelength will be a tradeoff between various aspects: e.g., penetration (transparency of intermediate layers), optical contrast of grating material versus surrounding material and spectral resolution (e.g., wavelengths close to pitch).

Further embodiments according to the invention are presented in below numbered clauses:
1. A method of performing a measurement in an inspection apparatus, comprising:

configuring one or more controllable characteristics of at least one driving laser pulse of a high harmonic generation radiation source to control an output emission spectrum of illumination radiation provided by the high harmonic generation radiation source; and illuminating a target structure with said illuminating radiation.

2. A method according to clause 1 wherein said configuring step comprises configuring one or more controllable characteristics of a driving laser pulse so that the output emission spectrum comprises a plurality of discrete harmonic peaks.

3. A method according to clause 2 wherein a bandwidth of each harmonic peak is smaller than 0.2 nm.

4. A method according to clause 2 or 3 wherein the spectral separation between adjacent harmonic peaks is greater than the bandwidth of the harmonic peaks.

5. A method according to any of clauses 2 to 4 wherein said configuring step comprises configuring a central wavelength of said driving laser pulse so as to control the wavelength of at least one of the harmonic peaks.

6. A method according to any of clauses 2 to 5 wherein said configuring step comprises configuring a central wavelength of said driving laser pulse so as to optimize the wavelength of at least one of the harmonics for maximum measurement sensitivity of said target structure.

7. A method according to clause 5 or 6 wherein the output emission spectrum comprises a plateau region having a plurality of said harmonic peaks which are of similar intensity and a cut of region where the intensity falls significantly for each successive harmonic peak; and said at least one of the harmonic peaks for which the wavelength is controlled/optimized is a harmonic peak in the plateau region.

8. A method according to any preceding clause wherein the intensity of said driving laser pulse is cyclic over time and said configuring step comprises configuring the number of cycles of said driving laser pulse to be greater than 15.

9. A method according to clause 8 wherein said configuring step comprises configuring the number of cycles of said driving laser pulse to be between 15 and 30

10. A method according to clause 1 wherein said configuring step comprises configuring a driving field of said high harmonic generation radiation source by configuring one or more controllable characteristics of a plurality of driving laser pulses, at least some of which, comprise different central wavelengths.

11. A method according to clause 10 wherein said driving laser pulses number three.

12. A method according to clause 10 or 11 wherein said configuring step comprises configuring said one or more controllable characteristics of the plurality of driving laser pulses so as to temporally shape a driving electric field of the high harmonic generation radiation source such that a narrow band of said output emission spectrum is enhanced and the remainder of the output emission spectrum is suppressed.

13. A method according to clause 12 wherein said enhancement of a narrow band is such that the output emission spectrum is substantially monochromatic.

14. A method according to clause 12 or 13 wherein the intensity of one of the plurality of driving laser pulses relative to one or more of the other of the plurality of driving laser pulses is varied to control a peak wavelength of said narrow band of the output emission spectrum which is enhanced.

15. A method according to clause 12, 13 or 14 wherein the intensity of one of the plurality of driving laser pulses relative to one or more of the other of the plurality of driving laser pulses is varied so as to optimize the peak wavelength of said narrow band of the output emission spectrum which is enhanced for maximum measurement sensitivity of said target structure.

16. A method according to any of clause 12 to 15 wherein said configuring step comprises configuring one or more controllable characteristics of the plurality of driving laser pulses such that a peak wavelength of said narrow band of the output emission spectrum which is enhanced is between 2 nm and 40 nm.

17. A method according to any of clause 12 to 16 wherein said configuring step comprises configuring one or more controllable characteristics of the plurality of driving laser pulses such that a peak wavelength of said narrow band of the output emission spectrum which is enhanced is between 9 nm and 15 nm.

18. A method according to any of clauses 10 to 17 wherein one of said plurality of driving laser pulses is obtained directly from a driving laser output and at least one other of said plurality of driving laser pulses is obtained by converting said driving laser output using a frequency converter element.

19. A method according to clause 18 wherein another of said plurality of driving laser pulses is obtained via optical parameter amplification.

20. A method according to any preceding clause comprising detecting scattered radiation from said illuminating of the target structure; and determining an overlay offset between different layers of said target structure from said scattered radiation.

21. An inspection apparatus comprising a high harmonic generation radiation source and operable to perform the method of any preceding clause.

22. A computer program product comprising machine readable instructions which, when run on a suitable processor, cause the processor to perform at least the configuring step in a method of any of clauses 1 to 20.

23. An inspection apparatus comprising a high harmonic generation radiation source, said high harmonic generation radiation source comprising a driving laser source operable to emit a driving laser pulse;

wherein one or more controllable characteristics of the driving laser pulse is configured such that that an output emission spectrum of the high harmonic generation radiation source comprises a plurality of discrete harmonic peaks.

24. An inspection apparatus according to clause 23 wherein a bandwidth of each harmonic peak is smaller than 0.2 nm.

25. An inspection apparatus according to clause 23 or 24 wherein the spectral separation between adjacent harmonic peaks is greater than the bandwidth of the harmonic peaks.

26. An inspection apparatus according to any of clauses 23 to 25 wherein a central wavelength of said driving laser pulse is configurable so as to control a wavelength of at least one of the harmonic peaks.

27. An inspection apparatus according to any of clauses 23 to 26 wherein a central wavelength of said driving laser pulse is configurable so as to optimize a wavelength of at least one of the harmonics for maximum measurement sensitivity of a target structure being measured.

28. An inspection apparatus according to clause 26 or 27 wherein the output emission spectrum comprises a plateau region having a plurality of said harmonic peaks which are of similar intensity and a cut of region where the intensity falls significantly for each successive harmonic peak; and said at least one of the harmonic peaks for which the wavelength is controlled/optimized is a harmonic peak in the plateau region.

29. An inspection apparatus according to any of clauses 23 to 28 wherein the intensity of said driving laser pulse is cyclic over time and the number of cycles of said driving laser pulse is greater than 15.

30. An inspection apparatus according to clause 29 wherein the number of cycles of said driving laser pulse is between 15 and 30.

31. An inspection apparatus comprising a high harmonic generation radiation source, said high harmonic generation radiation source comprising a plurality of driving laser sources, each being operable to emit a driving laser pulse with a different central wavelength.

32. An inspection apparatus according to clause 31 wherein said driving laser sources number three.

33. An inspection apparatus according to clause 31 or 32 wherein one or more controllable characteristics of each driving laser pulse is configured so as to temporally shape a driving electric field of the high harmonic generation radiation source such that a narrow band of an output emission spectrum of the high harmonic generation radiation source is enhanced and the remainder of the output emission spectrum is suppressed.

34. An inspection apparatus according to clause 33 wherein said one or more controllable characteristics of each driving laser pulse is configured such that said enhancement of a narrow band results in the output emission spectrum being substantially monochromatic.

35. An inspection apparatus according to clause 33 or 34 wherein the intensity of one of the plurality of driving laser pulses relative to one or more of the other of the plurality of driving laser pulses is configurable to control a peak wavelength of said narrow band of the output emission spectrum which is enhanced.

36. An inspection apparatus according to clause 33, 34 or 35 wherein an intensity of one of said driving laser pulses relative to one or more of the other of said driving laser pulses is configurable so as to optimize the peak wavelength of said narrow band of the output emission spectrum which is enhanced for maximum measurement sensitivity of a target structure being measured.

37. An inspection apparatus according to any of clauses 33 to 36 wherein the plurality of driving laser sources are configured such that a peak wavelength of said narrow band of the output emission spectrum which is enhanced is smaller than 20 nm.

38. An inspection apparatus according to any of clauses 33 to 36 wherein the plurality of driving laser sources are configured such that a peak wavelength of said narrow band of the output emission spectrum which is enhanced is in the region of 40 nm.

39. An inspection apparatus according to any of clauses 31 to 38 wherein the plurality of driving laser sources are derived from a single laser device, such that one of said driving laser sources is obtained from directly from the laser device output and at least one other of said driving laser sources is obtained by converting the laser device output using a frequency converter element.

40. An inspection apparatus according to clause 39 wherein another of said driving laser sources is obtained via optical parameter amplification of the laser device output.

41. A high harmonic generation radiation source comprising a plurality of driving laser sources, each being operable to emit a driving laser pulse with a different central wavelength.

42. A high harmonic generation radiation source according to clause 41 wherein said driving laser sources number three.

43. A high harmonic generation radiation source according to clause 41 or 42 wherein one or more controllable characteristics of each driving laser pulse is configured so as to temporally shape a driving electric field of the high harmonic generation radiation source such that a narrow band of an output emission spectrum of the high harmonic generation radiation source is enhanced and the remainder of the output emission spectrum is suppressed.

44. A high harmonic generation radiation source according to clause 43 wherein said one or more controllable characteristics of each driving laser pulse is configured such that said enhancement of a narrow band results in the output emission spectrum being substantially monochromatic.

45. A high harmonic generation radiation source according to clause 43 or 44 wherein the intensity of one of the plurality of driving laser pulses relative to one or more of the other of the plurality of driving laser pulses is configurable to control a peak wavelength of said narrow band of the output emission spectrum which is enhanced.

46. A high harmonic generation radiation source according to clause 43, 44 or 45, for an inspection apparatus, wherein an intensity of one of said driving laser pulses relative to one or more of the other of said driving laser pulses is configurable so as to optimize the peak wavelength of said narrow band of the output emission spectrum which is enhanced for maximum measurement sensitivity of a target structure being measured.

47. A high harmonic generation radiation source according to any of clauses 43 to 46 wherein the plurality of driving laser sources are configured such that a peak wavelength of said narrow band of the output emission spectrum which is enhanced is smaller than 20 nm.

48. A high harmonic generation radiation source according to any of clauses 43 to 46 wherein the plurality of driving laser sources are configured such that a peak wavelength of said narrow band of the output emission spectrum which is enhanced is in the region of 40 nm.

49. A high harmonic generation radiation source according to any of clauses 41 to 48 wherein the plurality of driving laser sources are derived from a single laser device, such that one of said driving laser sources is obtained from directly from the laser device output and at least one other of said driving laser sources is obtained by converting the laser device output using a frequency converter element.

50. A high harmonic generation radiation source according to clause 49 wherein another of said driving laser sources is obtained via optical parameter amplification of the laser device output.

51. A high harmonic generation radiation source comprising a driving laser source operable to emit a driving laser pulse; wherein one or more controllable characteristics of the driving laser pulse is configured such that that an output emission spectrum of the high harmonic generation radiation source comprises a plurality of discrete harmonic peaks.

52. A high harmonic generation radiation source according to clause 51 wherein a bandwidth of each harmonic peak is smaller than 0.2 nm.

53. A high harmonic generation radiation source according to clause 51 or 52 wherein the spectral separation between adjacent harmonic peaks is greater than the bandwidth of the harmonic peaks.

54. A high harmonic generation radiation source according to any of clauses 51 to 53 wherein a central wavelength of said driving laser pulse is configurable so as to control a wavelength of at least one of the harmonic peaks.

55. A high harmonic generation radiation source according to any of clauses 51 to 54, for an inspection apparatus, wherein a central wavelength of said driving laser pulse is configurable so as to optimize a wavelength of at least one of the harmonics for maximum measurement sensitivity of a target structure being measured.

56. A high harmonic generation radiation source according to clause 54 or 55 wherein the output emission spectrum comprises a plateau region having a plurality of said harmonic peaks which are of similar intensity and a cut of region where the intensity falls significantly for each successive harmonic peak; and said at least one of the harmonic peaks for which the wavelength is controlled/optimized is a harmonic peak in the plateau region.

57. A high harmonic generation radiation source according to any of clauses 51 to 56 wherein the intensity of said driving laser pulse is cyclic over time and the number of cycles of said driving laser pulse is greater than 15.

58. A high harmonic generation radiation source according to clause 57 wherein the number of cycles of said driving laser pulse is between 15 and 30.

Although specific reference may be made in this text to the use of lithographic apparatus in the manufacture of ICs, it should be understood that the lithographic apparatus described herein may have other applications, such as the manufacture of integrated optical systems, guidance and detection patterns for magnetic domain memories, flat-panel displays, liquid-crystal displays (LCDs), thin-film magnetic heads, etc. The skilled artisan will appreciate that, in the context of such alternative applications, any use of the terms "wafer" or "die" herein may be considered as synonymous with the more general terms "substrate" or "target portion", respectively. The substrate referred to herein may be processed, before or after exposure, in for example a track (a tool that typically applies a layer of resist to a substrate and develops the exposed resist), a metrology tool and/or an inspection tool. Where applicable, the disclosure herein may be applied to such and other substrate processing tools. Further, the substrate may be processed more than once, for example in order to create a multi-layer IC, so that the term substrate used herein may also refer to a substrate that already contains multiple processed layers.

Although specific reference may have been made above to the use of embodiments of the invention in the context of optical lithography, it will be appreciated that the invention may be used in other applications, for example imprint lithography, and where the context allows, is not limited to optical lithography. In imprint lithography a topography in a patterning device defines the pattern created on a substrate. The topography of the patterning device may be pressed into a layer of resist supplied to the substrate whereupon the resist is cured by applying electromagnetic radiation, heat, pressure or a combination thereof. The patterning device is moved out of the resist leaving a pattern in it after the resist is cured.

The terms "radiation" and "beam" used in relation to the lithographic apparatus encompass all types of electromagnetic radiation, including ultraviolet (UV) radiation (e.g., having a wavelength of or about 365, 355, 248, 193, 157 or 126 nm) and extreme ultra-violet (EUV) radiation (e.g., having a wavelength in the range of 5-20 nm), as well as particle beams, such as ion beams or electron beams.

The term "lens", where the context allows, may refer to any one or combination of various types of optical components, including refractive, reflective, magnetic, electromagnetic and electrostatic optical components.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description by example, and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

The invention claimed is:

1. A method of performing a measurement in an inspection apparatus, comprising:
configuring one or more controllable characteristics of at least one driving laser pulse of a high harmonic generation radiation source to control an output emission spectrum of illumination radiation provided by the high harmonic generation radiation source;
illuminating a target structure with the illuminating radiation;
detecting scattered radiation from the illuminating of the target structure; and
determining one or more of an overlay offset between different layers of the target structure, asymmetry, focus, or dose from the scattered radiation.

2. The method of claim 1, wherein the configuring step comprises configuring one or more controllable characteristics of a driving laser pulse so that the output emission spectrum comprises a plurality of discrete harmonic peaks.

3. The method of claim 2, wherein a bandwidth of each harmonic peak is smaller than 0.2 nm.

4. The method of claim 2, wherein the spectral separation between adjacent harmonic peaks is greater than the bandwidth of the harmonic peaks.

5. The method of claim 2, wherein the configuring step comprises configuring a central wavelength of the driving laser pulse so as to control the wavelength of at least one of the harmonic peaks.

6. The method of claim 2, wherein the configuring step comprises configuring a central wavelength of the driving laser pulse so as to optimize the wavelength of at least one of the harmonics for maximum measurement sensitivity of the target structure.

7. The method of claim 5, wherein the output emission spectrum comprises a plateau region having a plurality of the harmonic peaks which are of similar intensity and a cut-off region where the intensity falls significantly for each successive harmonic peak; and the at least one of the harmonic peaks for which the wavelength is controlled is a harmonic peak in the plateau region.

8. The method of claim 1, wherein the intensity of the driving laser pulse is cyclic over time and the configuring step comprises configuring the number of cycles of the driving laser pulse to be greater than 15.

9. The method of claim 8, wherein the configuring step comprises configuring the number of cycles of the driving laser pulse to be between 15 and 30.

10. The method of claim 1, wherein the configuring step comprises configuring a driving field of the high harmonic generation radiation source by configuring one or more controllable characteristics of a plurality of driving laser pulses, at least some of which, comprise different central wavelengths.

11. The method of claim 10, wherein the driving laser pulses number three.

12. The method of claim 10, wherein the configuring step comprises configuring the one or more controllable characteristics of the plurality of driving laser pulses so as to temporally shape a driving electric field of the high harmonic generation radiation source such that a narrow band of the output emission spectrum is enhanced and the remainder of the output emission spectrum is suppressed.

13. The method of claim 12, wherein the enhancement of a narrow band is such that the output emission spectrum is substantially monochromatic.

14. The method of claim 12, wherein the intensity of one of the plurality of driving laser pulses relative to one or more of the other of the plurality of driving laser pulses is varied to control a peak wavelength of the narrow band of the output emission spectrum which is enhanced.

15. The method of claim 12, wherein the intensity of one of the plurality of driving laser pulses relative to one or more of the other of the plurality of driving laser pulses is varied so as to optimize the peak wavelength of the narrow band of the output emission spectrum which is enhanced for maximum measurement sensitivity of the target structure.

16. The method of any of claim 12, wherein the configuring step comprises configuring one or more controllable characteristics of the plurality of driving laser pulses such that a peak wavelength of the narrow band of the output emission spectrum which is enhanced is between 2 nm and 40 nm.

17. The method of any of claim 12, wherein the configuring step comprises configuring one or more controllable characteristics of the plurality of driving laser pulses such that a peak wavelength of the narrow band of the output emission spectrum which is enhanced is between 9 nm and 15 nm.

18. An inspection apparatus, comprising:
a high harmonic generation radiation source;
a controller, coupled to the source, for configuring one or more controllable characteristics of at least one driving laser pulse of a high harmonic generation radiation source to control an output emission spectrum of illumination radiation provided by the high harmonic generation radiation source;
illuminating a target structure with the illuminating radiation;
detecting scattered radiation from the illuminating of the target structure; and
determining one or more of an overlay offset between different layers of the target structure, asymmetry, focus, or dose from the scattered radiation.

19. A non-transitory computer program product comprising machine readable instructions which, when run on a suitable processor, cause the processor to perform:
configuring one or more controllable characteristics of at least one driving laser pulse of a high harmonic generation radiation source to control an output emission spectrum of illumination radiation provided by the high harmonic generation radiation source;
illuminating a target structure with the illuminating radiation;
detecting scattered radiation from the illuminating of the target structure; and determining one or more of an overlay offset between different layers of the target structure, asymmetry, focus, or dose from the scattered radiation.

\* \* \* \* \*